US011420951B1

(12) United States Patent
Sheng

(10) Patent No.: US 11,420,951 B1
(45) Date of Patent: Aug. 23, 2022

(54) ETHYLENE OXIDE RECYCLING SYSTEM

(71) Applicant: Hangzhou Bocon Mechanical and Electrical Equipment Co., Ltd., Zhejiang (CN)

(72) Inventor: Qiping Sheng, Zhejiang (CN)

(73) Assignee: Hangzhou Bocon Mechanical and Electrical Equipment Co., Ltd., Hangzhou (CN)

( * ) Notice: Subject to any disclaimer, the term of this patent is extended or adjusted under 35 U.S.C. 154(b) by 0 days.

(21) Appl. No.: 17/669,346

(22) Filed: Feb. 10, 2022

(30) Foreign Application Priority Data

Jul. 30, 2021 (CN) .......................... 202110873264.8
Nov. 25, 2021 (CN) .......................... 202122915377.8

(51) Int. Cl.
*B01D 53/02* (2006.01)
*C07D 301/32* (2006.01)
*B01D 53/00* (2006.01)

(52) U.S. Cl.
CPC ......... *C07D 301/32* (2013.01); *B01D 53/002* (2013.01); *B01D 53/02* (2013.01); *B01D 2253/102* (2013.01); *B01D 2257/70* (2013.01)

(58) Field of Classification Search
CPC ................ C07D 301/32; B01D 53/002; B01D 2253/102; B01D 2257/70
See application file for complete search history.

(56) References Cited

U.S. PATENT DOCUMENTS

| 2,622,088 | A | * | 12/1952 | Thomas | C07D 301/32 549/534 |
| 2,775,600 | A | * | 12/1956 | Maslan | C07D 301/32 62/619 |
| 3,644,432 | A | * | 2/1972 | Gilman | C07D 301/32 549/541 |
| 3,989,461 | A | * | 11/1976 | Skocypec | A61L 2/206 422/111 |
| 9,616,143 | B2 | * | 4/2017 | Snyder | A61B 50/13 |
| 10,391,435 | B2 | * | 8/2019 | Turbett | A61L 2/26 |

FOREIGN PATENT DOCUMENTS

| CN | 209092758 U | 7/2019 |
| CN | 111269200 A | 6/2020 |

* cited by examiner

*Primary Examiner* — Christopher P Jones

(57) ABSTRACT

The present application relates to a field of ethylene oxide recycling system, which includes an EO sterilization module, an oil-gas separation module, a cooling separation module, a storage module and a vaporization circulation module. The oil-gas separation module used to separate oil from exhaust gas is connected with the EO sterilization module. The cooling separation module used for cooling the exhaust gas is connected with the oil-gas separation module. The storage module for storing the ethylene oxide is connected with the cooling separation module. The vaporization circulation module for vaporize the ethylene oxide is connected with the storage module. The vaporization circulation module is further connected with the EO sterilization module, so as to form a circulation.

8 Claims, 3 Drawing Sheets

ETHYLENE OXIDE RECYCLING SYSTEM

CROSS-REFERENCE TO RELATED APPLICATION

This application claims the priority and benefit of Chinese patent applications serial no. CN202110873264.8, filed on Jul. 30, 2021 and CN202122915377.8, filed on Nov. 25, 2021. The entirety of the above-mentioned patent applications are hereby incorporated by reference herein and made a part of this specification.

TECHNICAL FIELD

The present application relates to a field of the ethylene oxide recycling, and in particular, relates to an ethylene oxide recycling system.

BACKGROUND ART

Ethylene oxide (EO) is a board-spectrum sterilant, which can kill various microorganisms at room temperature. It has the following advantages: it can kill almost all microorganisms; the sterilized articles can be wrapped and integrally packed, so that the articles can remain a sterile state before use; comparatively, EO does not corrode plastics, metals and rubber, so that the articles will not turn yellow and brittle; it can penetrate irregular objects to achieve sterilization; and it can be used for sterilization of the articles that cannot be sterilized by disinfectant immersion, dry heat sterilization, pressure sterilization, vapor sterilization and other chemical gases sterilization. Therefore, EO sterilization device is a key equipment of the disposable sterile medical apparatus manufacturers.

In existing technologies, the ethylene oxide in the EO sterilization cabinet used for disinfection and sterilization should be recirculated by a recycling system. On one hand, it can reduce the waste of the ethylene oxide; and, on the other hand, it can reduce the pollution to the environment as well. However, in existing technologies, the ethylene oxide is generally recirculated by means of freezion and compression, in which the recycling rate is relatively low and a relatively large amount of the ethylene oxide may escape in the recycling process.

SUMMARY

In order to solve the above problems, the present application provides an ethylene oxide recycling system.

An ethylene oxide recycling system includes a EO sterilization cabinet, a vacuum pump, an oil-gas separator, a primary freezing tower, a secondary freezing tower, a compression pump, a mist eliminator, an activated carbon adsorption tank and an EO storage tank;

an exhaust outlet of the EO sterilization cabinet is connected with an inlet of the vacuum pump through vacuum valve; an oil-gas outlet of the vacuum pump is connected with an inlet of the oil-gas separator; a primary cooling coil is provided in the primary freezing tower; a top outlet of the oil-gas separator is connected with a first port of a first pneumatic three-way ball valve; a second port of the first pneumatic three-way ball valve is connected with a exhaust gas treatment unit; a third port of the pneumatic three-way ball valve is connected with a top end of the primary cooling coil; a secondary cooling coil is provided in the secondary freezing tower; a bottom end of the primary cooling coil is connected with an inlet of a first pneumatic straight through ball valve; two by-passes are provided at an outlet of the first pneumatic straight through ball valve, one by-pass is connected with a top end of the secondary cooling coil, and the other by-pass is connected with an outlet of the compression pump; a bottom end of the secondary cooling coil is connected with an inlet of the mist eliminator; two by-passes are provided at an outlet of the mist eliminator, one by-pass is connected with a first port of a second pneumatic three-way ball valve, and the other by-pass is connected with an inlet of an inlet of a second pneumatic straight through ball valve; a second port of the second pneumatic three-way ball valve is connected with a bottom of the activated carbon adsorption tank; a third port of the second pneumatic three-way ball valve is connected with an inlet of the compression pump; two by-passes are provided at a top of the activated carbon adsorption tank, one by-pass is connected with an outlet of the second pneumatic straight through ball valve and the other by-pass is connected with the exhaust gas treatment unit through a third pneumatic straight through ball valve; an inlet on the top left of the EO storage is connected with the bottom of the secondary cooling coil; two by-passes are provided at an outlet on the bottom of the EO storage tank, one by-pass is connected with a waste liquid storage tank, and the other by-pass is connected with an gas inlet of the EO sterilization cabinet through a fifth pneumatic straight through ball valve; the bottom of the primary cooling coil is connected with the waste liquid storage tank through a sixth pneumatic straight through ball valve; and a bottom of the oil-gas separator is connected with a liquid storage tank through a manual valve.

An ethylene oxide recycling system includes a sterilization cabinet, a vacuum pump, an oil-gas separator, a gas-liquid separator, a booster pump, a condensing tower, a storage tank, a freezing machine and a circulation pump; an exhaust outlet of the sterilization cabinet is connected with an inlet of the vacuum pump through vacuum valve; an oil-gas outlet of the vacuum pump is connected with a top of the oil-gas separator; a return port of the vacuum pump is connected with a bottom of the oil-gas separator; a top outlet of the oil-gas separator is connected with an inlet of the gas-liquid separator; an outlet of the gas-liquid separator is connected with a left inlet of the condensing tower through the booster pump; a bottom inlet of the condensing tower is connected with the storage tank, an outlet of the storage tank is connected with a gas inlet of the sterilization cabinet; the oil-gas separator, the gas-liquid separator and the condensing tower are all provided with a cooling coil; an inlet of the circulation pump is connected with an outlet of the freezing machine; an outlet of the circulation pump is connected with one end of each cooling coil; and the other end of each cooling coil is connected with an inlet of the freezing machine.

DETAILED DESCRIPTION

The present application is further described in detail below in combination with Figures.

Embodiment 1

Figure 1:
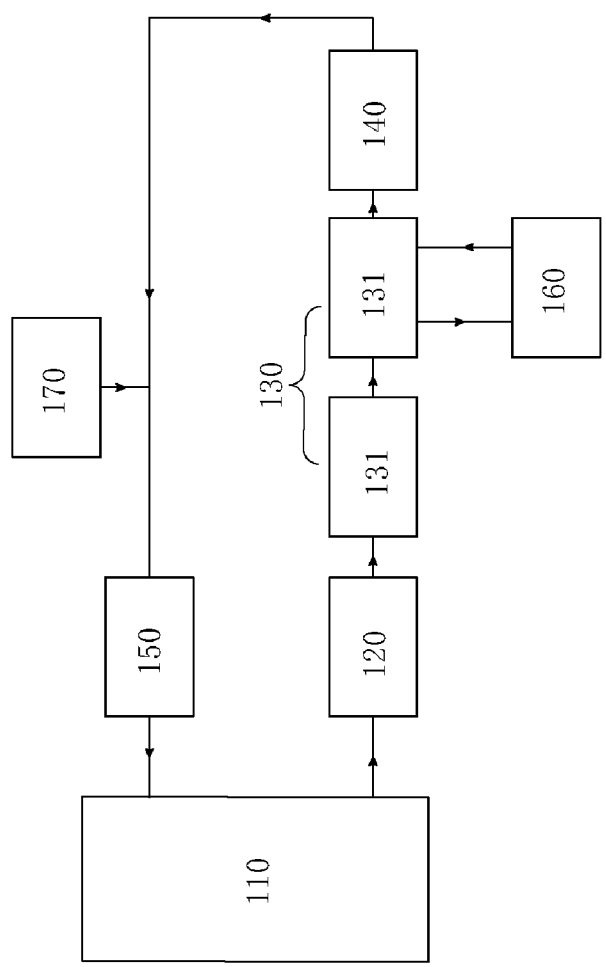
FIG. 1 is a structural diagram of an ethylene oxide recycling system in Embodiment 1.

Referring to FIG. 1, an ethylene oxide recycling system includes an EO sterilization module 110, an oil-gas separation module 120, a cooling separation module 130, a storage module 140, a vaporization circulation module 150, an adsorption circulation module 160 and a gas mixing module 170.

The EO sterilization module 110, the oil-gas separation module 120, the cooling separation module 130, the storage module 140 and the vaporization circulation module 150 are connected with each other successively, and the vaporization circulation module 150 is also connected with the EO sterilization module 110, so as to form a circulation. The adsorption circulation module 160 is connected with the cooling separation module 130. The gas mixing module 170 is connected with the vaporization circulation module 150. The cooling separation module 130 includes a plurality of coolers 131 in a serial connection.

The implementation principle of Embodiment 1 is as follow. The EO sterilization module 110 can be used for disinfection and sterilization. After the disinfection and sterilization, the exhaust gas from the EO sterilization module 110 enters the oil-gas separation module 120 together with the oil, the oil and the exhaust gas are separated by oil-gas separation module 120, the oil stays in the oil-gas separation module 120, while the exhaust gas enters the cooling separation module 130. The exhaust gas is frozen and compressed by a plurality of coolers 131 in a serial connection. After cooling and compression, a majority of the ethylene oxide is stored in the storage module 140. A minority of the ethylene oxide enters the adsorption circulation module 160. The adsorption circulation module 160 is provided with a substance capable of adsorbing ethylene oxide, such as activated carbon. After switching the path, the ethylene oxide adsorbed in the adsorption circulation module 160 can be desorbed and sent back into the cooling separation module 130. The recycling rate of the ethylene oxide can be continuously increased by repeating the above processes. The ethylene oxide and the gas like nitrogen or carbon dioxide can be mixed in the gas mixing module 170, and the mixed gas is vaporized by the vaporization circulation module 150 and be transported into the EO sterilization module 110 for recycling.

Embodiment 2

Figure 2:
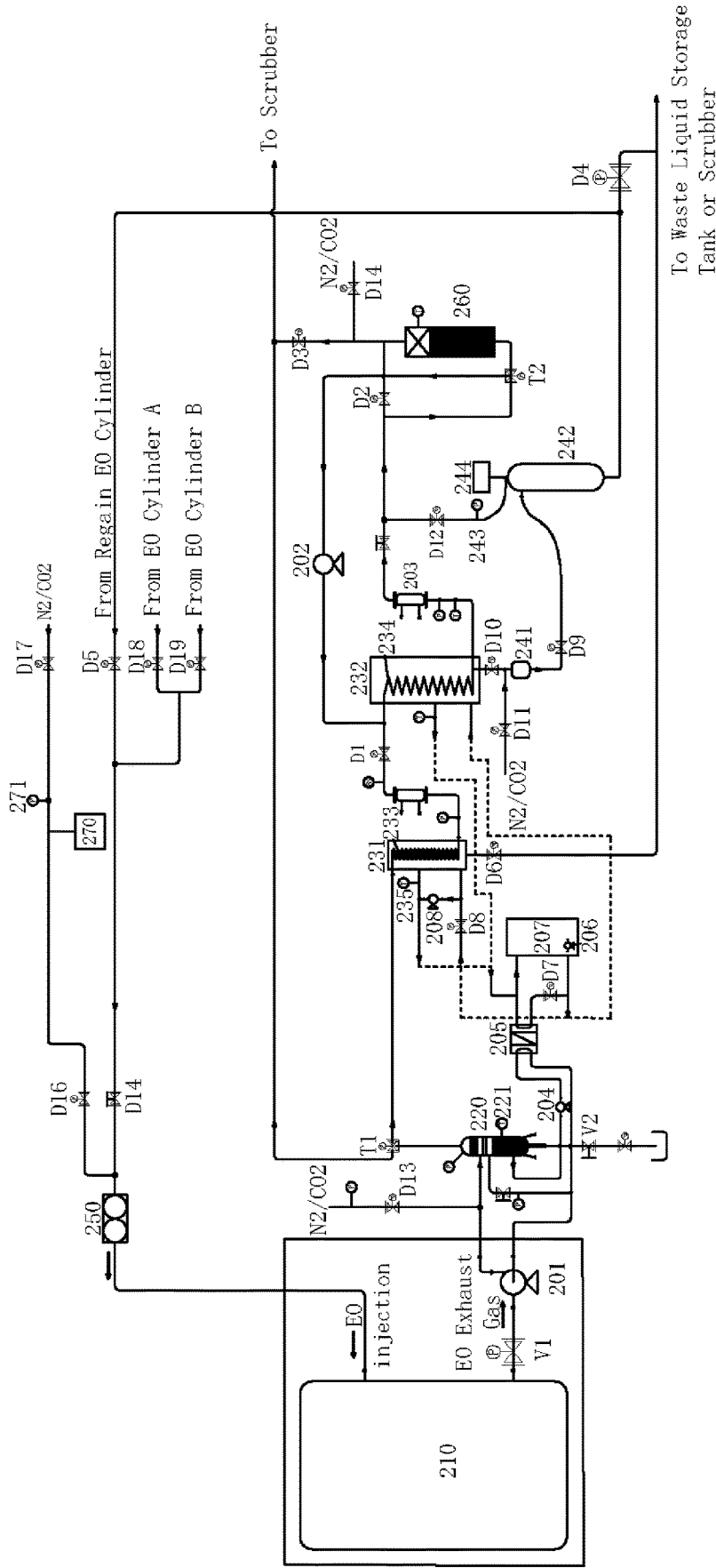
FIG. 2 is a structural diagram of an ethylene oxide recycling system in Embodiment 2.

Referring to FIG. 2, an ethylene oxide recycling system includes an EO sterilization cabinet 210, a vacuum pump 201, an oil-gas separator 220, a primary freezing tower 231, a secondary freezing tower 232, a compression pump 202, a mist eliminator 203, an activated carbon adsorption tank 260 and an EO storage tank 242.

An exhaust outlet of the EO sterilization cabinet 210 is connected with an inlet of the vacuum pump 201 through vacuum valve V1. An oil-gas outlet of the vacuum pump 201 is connected with an inlet of the oil-gas separator 220. A primary cooling coil 233 is provided in the primary freezing tower 231. A top outlet of the oil-gas separator 220 is connected with a first port of a first pneumatic three-way ball valve T1, a second port of the first pneumatic three-way ball valve T1 is connected with an exhaust gas treatment unit, and a third port of the pneumatic three-way ball valve T1 is connected with a top end of the primary cooling coil 233. A secondary cooling coil 234 is provided in the secondary freezing tower 232. A bottom end of the primary cooling coil is connected with an inlet of a first pneumatic straight through ball valve D1, two by-passes are provided at an outlet of the first pneumatic straight through ball valve D1, one by-pass is connected with a top end of the secondary cooling coil 234 and the other by-pass is connected with an outlet of the compression pump 202. A bottom end of the secondary cooling coil 234 is connected with an inlet of the mist eliminator 203, two by-passes are provided at an outlet of the mist eliminator 203, one by-pass is connected with a first port of a second pneumatic three-way ball valve T2, and the other by-pass is connected with an inlet of an inlet of a second pneumatic straight through ball valve T2. A second port of the second pneumatic three-way ball valve T2 is connected with a bottom of the activated carbon adsorption tank 260, and a third port of the second pneumatic three-way ball valve T2 is connected with an inlet of the compression pump 202. Two by-passes are provided at a top of the activated carbon adsorption tank 260, in which one by-pass is connected with an outlet of the second pneumatic straight through ball valve D2 and the other by-pass is connected with the exhaust gas treatment unit through a third pneumatic straight through ball valve D3. An inlet on the top left of the EO storage tank 242 is connected with the bottom of the secondary cooling coil 234. Two by-passes are provided at an outlet on the bottom of the EO storage tank 242, one by-pass is connected with a waste liquid storage tank through a fourth pneumatic straight through ball valve D4, and the other by-pass is connected with a gas inlet of the EO sterilization cabinet 210 through a fifth pneumatic straight through ball valve D5. The bottom of the primary cooling coil 233 is connected with the waste liquid storage tank through a sixth pneumatic straight through ball valve D6. And a bottom of the oil-gas separator 220 is connected with a liquid storage tank through manual valve V2.

A first circulation pump 204, a heat exchanger 205, a second circulation pump 206 and a freezing machine 207 are also included. An inlet of the first circulation pump 204 is connected with an oil outlet of the oil-gas separator 220, an outlet of the first circulation pump 204 is connected with an oil inlet of the oil-gas separator 220 and an oil inlet of the vacuum pump 201. An outlet pipeline of the first circulation pump 204 passes through a left heat exchange chamber of the heat exchanger 205. An inlet of the second circulation pump 206 is connected with a coolant liquid outlet of the freezing machine 207. Two by-passes are provided at an outlet of the second circulation pump 206, in which one by-pass is connected with an inlet of a seventh pneumatic straight through ball valve D7, and the other by-pass is connected with coolant liquid inlets of the primary freezing tower 231 and the secondary freezing tower 232. An outlet pipeline of the seventh pneumatic straight through ball valve D7 passes through a right heat exchanger chamber of the heat exchanger 205 and is connected with a coolant liquid inlet of the freezing machine 207. Coolant liquid outlets of the primary freezing tower 231 and the secondary freezing tower 232 are also connected with the coolant liquid inlet of the freezing machine 207.

A coolant liquid inlet of the primary freezing tower 231 is connected with an outlet of the second circulation pump 206 through an eighth pneumatic straight through ball valve D8. A bottom end of the eighth pneumatic straight through ball valve D8 is connected with an inlet of a third circulation pump 208, an outlet of the third circulation pump 208 is connected with the coolant liquid outlet of the primary freezing tower 231. A first temperature sensor 235 is provided at an outlet of the primary freezing tower 231.

An inlet on the top left of the EO storage tank 242 is connected with the bottom of the secondary cooling coil 234 through a ninth pneumatic straight through ball valve D9, an EO buffer tank 241 and a tenth pneumatic straight through ball valve D10 successively. The position between the EO buffer tank 241 and the tenth pneumatic straight through ball valve D10 is also connected with a nitrogen storage tank through eleventh pneumatic straight through ball valve D11. A top inlet of the EO storage tank 242 is also connected with an outlet of the mist eliminator 203 through a first pressure sensor 243 and a twelfth pneumatic straight through ball valve D12. A suspended electronic scale 244 is provided on a top of the EO storage tank 242.

A connecting pipeline between an oil outlet of the vacuum pump 201 and the oil-gas separator 220 is connected with a nitrogen storage tank through a thirteenth pneumatic straight through ball valve D13. And a top of the activated carbon adsorption tank 260 is also connected with the nitrogen storage tank through a fourteenth pneumatic straight through ball valve D14.

A fifth pneumatic straight through ball valve D5 is connected with the gas inlet of the EO sterilization cabinet 210 through a fifteenth pneumatic straight through ball valve D15 and a vaporizer 250. A sixteenth pneumatic straight through ball valve D16 is connected between the vaporizer 250 and the fifteenth pneumatic straight through ball valve D15. The sixteenth pneumatic straight through ball valve D16 is connected with a nitrogen storage tank through a seventeenth pneumatic straight through ball valve D17. A mixing tank 270 and a second pressure sensor 271 are also provided between the sixteenth pneumatic straight through ball valve D16 and the seventeenth pneumatic straight through ball valve D17, and a position between the fifth pneumatic straight through ball valve D5 and the fifteenth pneumatic straight through ball valve D15 is also connected with a EO steel cylinder through an eighteenth pneumatic straight through ball valve D18 and a nineteenth pneumatic straight through ball valve D19.

A second temperature sensor 221 is provided at the oil-gas separator 220.

The implementation principle of Embodiment 2 is as follows. After the disinfection and sterilization operation of the EO sterilization cabinet 210, the vacuum valve V1 is opened and the vacuum pump 201 is started. The exhaust gas from the EO sterilization cabinet 210 enters the oil-gas separator 220 together with the oil, the oil and the exhaust gas are separated by oil-gas separator 220, the oil stays in the oil-gas separator 220, while the exhaust gas enters the primary cooling coil 233 through the first pneumatic three-way ball valve T1. When the pressure at the oil-gas separator 220 is too high, the paths of the first pneumatic three-way ball valve T1 can also be switched, so that the exhaust gas can be directly discharged to the exhaust gas treatment unit for purification treatment.

Waste liquid is generated from the exhaust gas in the primary cooling coil 233 generates after freezion and compression, and transported to the waste liquid storage tank through a sixth pneumatic straight through ball valve D6. The exhaust gas in the primary cooling coil 233 is transported to the secondary cooling coil 234 through a first pneumatic straight through ball valve D1.

The second circulation pump 206 can pump one portion of the coolant liquid into the primary freezing tower 231 and secondary freezing tower 232, and pump the other portion of the coolant liquid into the right heat exchange chamber of the heat exchanger 205, in which the coolant liquid then flows back to the freezing machine 207 for cooling, and the coolant liquid in the primary freezing tower 231 and secondary freezing tower 232 flows back to the freezing machine 207 for cooling. The coolant liquid in the primary freezing tower 231 and secondary freezing tower 232 freezes and compresses the fluid exhaust gas in the primary cooling coil 233 and the secondary cooling coil 234.

The first circulation pump 204 pumps the oil in the oil-gas separator 220 into the left heat exchange chamber of the heat exchanger 205 to exchange heat with the coolant liquid flowing in the right heat exchange chamber of the heat exchanger 205, so as to reduce the temperature of the oil. One portion of the oil with lower temperature flows back to the oil-gas separator 220, and the other flows into the vacuum pump 201 and is mixed with the exhaust gas from the EO sterilization cabinet 210, so as to cool the exhaust gas initially.

The exhaust gas contains some water vapor, therefore, the oil-gas separator 220 contains a portion of water in addition to the oil. When the oil-gas separator 220 contains relatively much water, the manual valve V2 is opened so that the oil-water mixture is drained into the liquid storage tank, and the oil-gas separator 220 is replenished with new oil.

When the exhaust gas is transported to the oil-gas separator 220 by vacuum pump 201, a thirteen pneumatic straight through ball valve can be opened to transport the inert nitrogen from the external nitrogen storage tank, so that the exhaust gas in the oil-gas separator 220 includes a portion of inert nitrogen, which increase the safety during the separation of the oil and gas.

When the temperature of the coolant liquid in the primary freezing tower 231 is too low, there is relatively much settled liquid, and excessive ethylene oxide may be settled and discharged into the waste liquid storage tank. The temperature of the coolant liquid at the outlet of the primary freezing tower 231 can be monitored by the first temperature sensor 235. When the temperature of the coolant liquid is too low, the eighth pneumatic straight through ball valve is closed. At this time, the external coolant liquid cannot enter into the primary freezing tower 231, and the coolant liquid in the primary freezing tower 231 can be self-circulated through the third circulation pump 208. On the contrary, when the temperature in the primary freezing tower 231 is high, the eighth pneumatic straight through ball valve is opened and the external coolant liquid is filled therethrough. At this time, the third circulation pump 208 can make the temperature of the coolant liquid in the primary freezing tower 231 more uniform.

After the exhaust gas in the secondary cooling coil 234 is frozen and compressed, a majority of the ethylene oxide enters and stores in the EO buffer tank 241 through the tenth pneumatic straight through ball valve D10, and a minority of the ethylene oxide and the exhaust gas enter the bottom of the activated carbon adsorption tank 260 through the mist eliminator 203 and the second pneumatic three-way ball valve T2, and is transported from bottom to top in the activated carbon adsorption tank 260, in which the ethylene oxide is adsorbed in the activated carbon adsorption tank 260 and the exhaust gas is discharged to the exhaust gas treatment unit through the third pneumatic straight through ball valve D3.

Then, the second pneumatic three-way ball valve T2 switches the paths, so that the compression pump 202 is started, and the first pneumatic straight through ball valve D1 is closed. The ethylene oxide adsorbed in the activated carbon adsorption tank 260 is desorbed by the compression pump 202, transported to the primary freezing tower 231, freezed and compressed continuously. At this time, the second pneumatic straight through ball valve D2 is opened, the ethylene oxide and exhaust gas from the primary freezing tower 231 enter the activated carbon adsorption tank 260 from the top thereof and back flushes the activated carbon adsorption tank 260, which are repeated so as to increase the recycling rate of the ethylene oxide continuously.

Since the ethylene oxide is adsorbed, a negative pressure is formed in the pipeline. At this time, the fourteenth pneumatic straight through ball valve D14 can be opened to refill gas in the pipeline.

When there is too much ethylene oxide in the EO buffer tank 214, the tenth pneumatic straight through ball valve D10 is closed and the nineth pneumatic straight through ball valve D9 is opened, so that the ethylene oxide in the EO buffer tank 241 enters the EO storage tank 242 and is stored therein. In order to avoid the situation that the ethylene oxide cannot be discharged from the EO buffer tank 241, the eleventh pneumatic straight through ball valve D11 is opened to fill in nitrogen, and flush the ethylene oxide from the EO buffer tank 241 into the EO storage tank 242 by nitrogen.

The seventeenth pneumatic straight through ball valve is opened and the sixteenth pneumatic straight through ball valve D16 is closed. The nitrogen is filled into the mixing tank 270. The gas pressure is monitored by the second pressure sensor 271. When the pressure reaches a threshold, the seventeenth pneumatic straight through ball valve is closed. When it is required to fill the ethylene oxide in the EO sterilization cabinet, the fifth pneumatic straight through ball valve D5 and the fifteenth pneumatic straight through ball valve D15 are opened to transport the ethylene oxide to the vaporizer 250, and the eighteenth pneumatic straight through ball valve D18 and the nineteenth pneumatic straight through ball valve D19 are opened to fill the ethylene oxide. Then, the sixteenth pneumatic straight through ball valve D16 is opened, the ethylene oxide is vaporized in the vaporizer 250 and the vaporized ethylene oxide is transported into the EO sterilization cabinet through the gas inlet.

Embodiment 3

Figure 3:
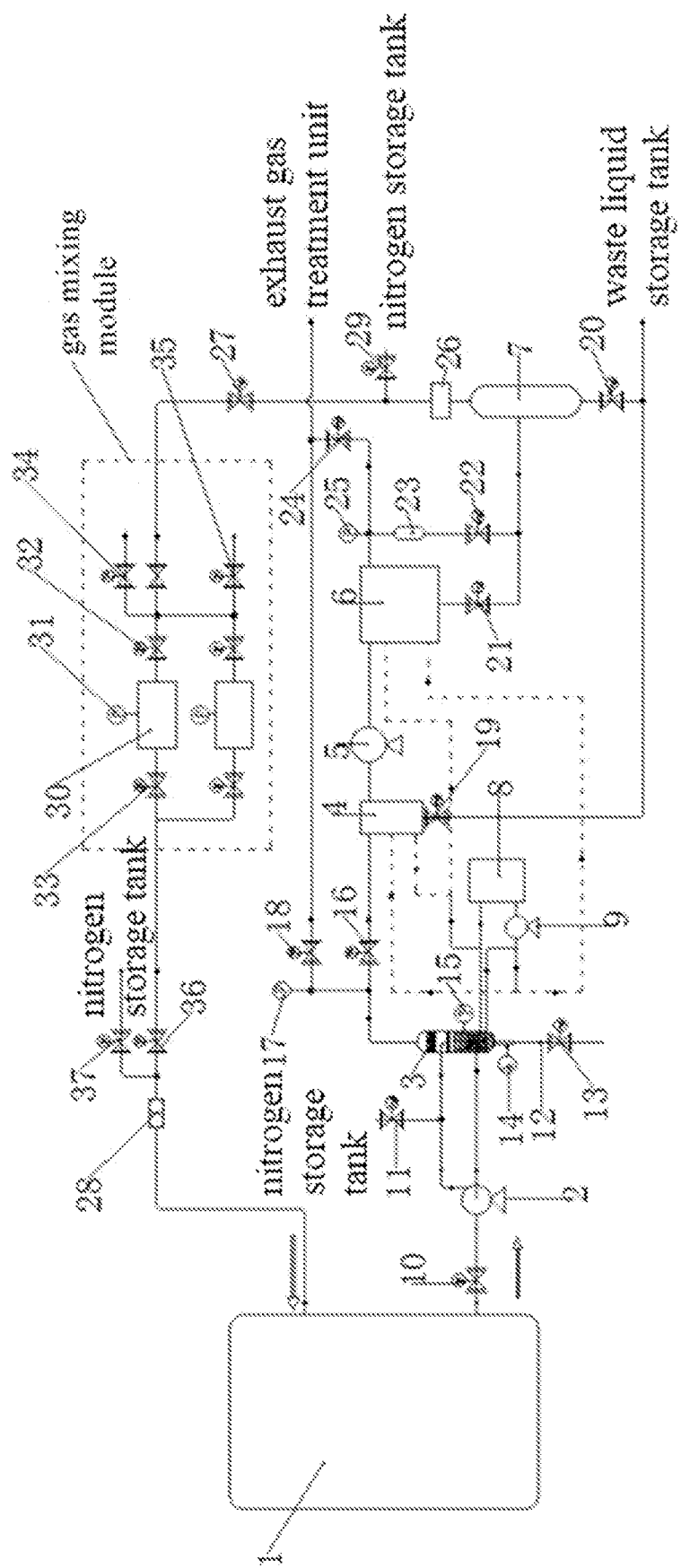
FIG. 3 is a structural diagram of an ethylene oxide recycling system in Embodiment 3.

Referring to FIG. 3, the ethylene oxide recycling system includes a sterilization cabinet 1, a vacuum pump 2, an oil-gas separator 3, a gas-liquid separator 4, a booster pump 5, a condensing tower 6, a storage tank 7, a freezing machine 8 and a circulation pump 9. An exhaust outlet of the sterilization cabinet 1 is connected with an inlet of the vacuum pump 2 through vacuum valve 10. An oil-gas outlet of the vacuum pump 2 is connected with a top of the oil-gas separator 3. A return port of the vacuum pump 2 is connected with a bottom of the oil-gas separator 3. A top outlet of the oil-gas separator 3 is connected with an inlet of the gas-liquid separator 4. An outlet of the gas-liquid separator 4 is connected with a left inlet of the condensing tower 6 through the booster pump 5. A bottom inlet of the condensing tower 6 is connected with the storage tank 7, and an outlet of the storage tank 7 is connected with a gas inlet of the sterilization cabinet 1. The oil-gas separator 3, the gas-liquid separator 4 and the condensing tower 6 are all provided with a cooling coil. An inlet of the circulation pump 9 is connected with an outlet of the freezing machine 8, and an outlet of the circulation pump 9 is connected with one end of each cooling coil. The other end of each cooling coil is connected with an inlet of the freezing machine 8.

A connecting pipeline between the oil outlet of the vacuum pump 2 and the oi-and-gas separator 3 is connected with an external nitrogen storage tank through A1 pneumatic ball valve 11.

A drainage pipeline 12 is provided at a bottom of the oil-gas separator 3. An First pneumatic ball valve 13 is provided in the drainage pipeline 12. A condensate water level electrode 14 is provided in the drainage pipeline 12 above the First pneumatic ball valve 13. A temperature sensor 15 is provided in the oil-gas separator 3.

A Second pneumatic ball valve 16 is provided in a connecting pipeline between the oil-gas separator 3 and the gas-liquid separator 4. The connecting pipeline between the Second pneumatic ball valve 16 and the oil-gas separator 3 is connected with an external exhaust gas treatment unit through a First pressure sensor 17 and a Third pneumatic ball valve 18 successively.

The bottom of the gas-liquid separator 4 is connected with an external waste liquid storage tank through C1 pneumatic ball valve 19. The bottom of the storage tank 7 is connected with the external waste liquid storage tank through D4 pneumatic ball valve 20.

A Fourth pneumatic ball valve 21 is provided in a connecting pipeline between a bottom of the condensing tower 6 and an inlet of the storage tank 7. A connecting pipeline between the Fourth pneumatic ball valve and the storage tank 7 is connected with a surge tank 23 through Fifth pneumatic ball valve 22. Two by-passes are provided on a top of the surge tank 23, one by-pass is connected with a right side of the condensing tower 6, and the other by-pass is connected with the external exhaust gas treatment unit through Sixth pneumatic ball valve 24. A Second pressure sensor is provided in a connecting pipeline between the condensing tower 6 and the surge tank 23.

A top outlet of the storage tank 7 is connected with a gas mixing module through suspended electronic scale 26 and a Seventh pneumatic ball valve 27 successively. The gas mixing module is connected with a gas inlet of the sterilization cabinet 1 through a vaporizer 28, and a position between the Seventh pneumatic ball valve and the suspended electronic scale 26 is connected with an external nitrogen storage tank through Eighth pneumatic ball valve 29.

The gas mixing module includes two mixers 30 disposed side by side. Each mixer 30 is provided with a P3 pressure sensor 31. An E1 pneumatic ball valve 32 and an E2 pneumatic ball valve 33 are connected at the upstream and downstream of each mixer 30 respectively. Two E1 pneumatic ball valve 32 are connected by a pipeline. Three by-passes are provided in this pipeline, in which one by-pass is connected with a Seventh pneumatic ball valve 27, and the other two by-passes are connected with an external EO steel cylinder and an external nitrogen storage tank respectively through E3 pneumatic ball valve 34 and E4 pneumatic ball valve 35. Two E2 pneumatic ball are commonly connected with the vaporizer 28.

A F1 pneumatic ball valve 36 is provided in a connecting pipeline between the vaporizer 28 and the E2 pneumatic ball valve. The position between the F1 pneumatic ball valve 36 and the vaporizer 28 is connected with an external nitrogen storage tank.

The implementation principle of Embodiment 3 is as follows. After the disinfection and sterilization operation of the cabinet 1, the vacuum valve 10 is opened. The vacuum pump 2 is started to vacuumize the sterilization cabinet 1. The exhaust gas from the sterilization cabinet 1 enters the oil-gas separator 3 together with the oil, the oil and the exhaust gas are separated by oil-gas separator 3, in which the oil stays in the oil-gas separator 3 and flows back to the vacuum pump 2 for recycling. In this process, the coolant liquid flows in the cooling coil of the oil-gas separator 3 are driven by the circulation pump 9. The coolant liquid is cooled by a freezing machine 8, so that the coolant liquid entering the oil-gas separator 3 has a relative low temperature, which can cool the oil. The oil with a relative low temperature is mixed with the exhaust gas at the vacuum pump 2, so as to initially cool the exhaust gas.

When the exhaust gas is transported to the oil-gas separator 3 through vacuum pump 2, the A1 pneumatic ball valve 11 can be opened, so that the exhaust gas can be replaced with nitrogen through the external nitrogen storage tank, which increases the safety during the oil-gas separation. The exhaust gas includes water vapor, therefore, a portion of water in addition to the oil is deposited in the oil-gas separator. The condensate water level electrode 14 can monitor the liquid height in the oil-gas separator. When the liquid height reach the threshold, the oil-water mixture can be drained by opening First pneumatic ball valve 13, and new oil is refilled.

The temperature sensor 15 can monitor the liquid temperature in the oil-gas separator. When the temperature is relatively high, the flow rate of the coolant liquid in the oil-gas separator can be increased by increasing the power of the circulation pump 9, so as to keep the oil within an appropriate temperature range.

After the processing by the oil-gas separator, the exhaust gas enters the gas- and liquid separator 4, and the water vapor and the exhaust gas are separated by the gas-liquid separator 4. The coolant liquid is circulated in the gas-liquid separator 4 by circulation pump 9, so as to cool the exhaust gas for a second time.

The First pressure sensor 17 can monitor the pressure at the oil-gas separator 3, and the Third pneumatic ball valve 18 is normally closed. When the pressure is too high, the Third pneumatic ball valve 18 can be opened to discharge the gas. The discharged exhaust gas is transported to the external exhaust gas treatment unit for processing.

The exhaust gas separated by the gas-liquid separator 4 is transported to the condensing tower 6 through the booster pump 5. The coolant liquid is circulated in the condensing tower 6 by the circulation pump 9, so as to cool the exhaust gas for a third time. The exhaust gas entered into the condensing tower 6 can be compressed by providing the booster pump 5, so as to improve the cooling effect in the condensing tower 6.

The surge tank 23 can be used to adjust the gas pressure in the condensing tower 6, that is, when the pressure in the condensing tower 6 is too high, a portion of the exhaust gas enters the surge tank 23. When the pressure in the condensing tower 6 is low, the exhaust gas in the surge tank can be filled into the condensing tower 6. The gas pressure in the condensing tower 6 can be in a dynamic equilibrium by providing the surge tank 23.

The EO gas condensed by the condensing tower 6 can enter the storage tank 7 and be stored therein. Second pressure sensor 25 can monitor the pressures at the condensing tower 6 and the surge tank 23. When the pressure is too high, the Sixth pneumatic ball valve 24 can be opened to discharge the gas. The waste liquid in the gas-liquid separator 4 and the storage tank 7 is drained into an external waste liquid storage tank by opening the C1 pneumatic ball valve 19 and the Fifth pneumatic ball valve 22.

When the sterilization cabinet 1 is required to conduct a next sterilization operation, the Seventh pneumatic ball valve 27 is opened to discharge the gas. The EO gas in the storage tank 7 is discharged through the suspended electronic scale 26, the suspended electronic scale 26 weights the discharged gas. The Eighth pneumatic ball valve 29 can be opened, so as to fill and replace the nitrogen through the external nitrogen storage tank, which increase the safety.

When the gas in the storage tank 7 is not enough, the E3 pneumatic ball valve 34 is opened to supple EO gas from an external EO steel cylinder. And the EO gas is mixed with the nitrogen by opening the E4 pneumatic ball valve 35. The mixed gas enters two mixer 30 for mixing, and is transported to the vaporizer 28 for vaporization. The replacement and addition of nitrogen are further carried out by opening F2 pneumatic ball valve 37.

The vaporized mixture of the EO and the nitrogen enters the sterilization cabinet 1 for sterilization. Carbon dioxide can be used as a substitute for nitrogen in this application.

The above are the preferred embodiments of the present application, which are not intend to limit the protection scope of the present application. Therefore, all equivalent changes made according to the structure, shape and principle of the present application should be covered within the protection scope of the present application.

What is claimed is:

1. An ethylene oxide (EO) recycling system comprising: an EO sterilization cabinet, a vacuum pump, an oil-gas separator, a primary freezing tower, a secondary freezing tower, a compression pump, a mist eliminator, an activated carbon adsorption tank and an EO storage tank;

an exhaust outlet of the EO sterilization cabinet is connected with an inlet of the vacuum pump through a vacuum valve; an oil-gas outlet of the vacuum pump is connected with an inlet of the oil-gas separator; a primary cooling coil is provided in the primary freezing tower; a top outlet of the oil-gas separator is connected with a first port of a first pneumatic three-way ball valve; a second port of the first pneumatic three-way ball valve is connected with an exhaust gas treatment unit; a third port of the pneumatic three-way ball valve is connected with a top end of the primary cooling coil; a secondary cooling coil is provided in the secondary freezing tower; a bottom end of the primary cooling coil is connected with an inlet of a first pneumatic straight through ball valve; two by-passes are provided at an outlet of the first pneumatic straight through ball valve, wherein one by-pass is connected with a top end of the secondary cooling coil and the other by-pass is connected with an outlet of the compression pump; a bottom end of the secondary cooling coil is connected with an inlet of the mist eliminator; two by-passes are provided at an outlet of the mist eliminator, wherein one by-pass is connected with a first port of a second pneumatic three-way ball valve, and the other by-pass is connected with an inlet of a second pneumatic straight through ball valve; a second port of the second pneumatic three-way ball valve is connected with a bottom of the activated carbon adsorption tank; a third port of the second pneumatic three-way ball valve is connected with an inlet of the compression pump; two by-passes are provided at a top of the activated carbon adsorption tank, wherein one by-pass is connected with an outlet of the second pneumatic straight through ball valve and the other by-pass is connected with the exhaust gas treatment unit through a third pneumatic straight through ball valve; an inlet on the top left of the EO storage tank is connected with the bottom of the secondary cooling coil; two by-passes are provided at an outlet on the bottom of the EO storage tank, wherein one by-pass is connected with a waste liquid storage tank through a fourth pneumatic straight through ball valve, and the other by-pass is connected with a gas inlet of the EO sterilization cabinet through a fifth pneumatic straight through ball valve; the bottom of the primary cooling coil is connected with the waste liquid storage tank through a sixth pneumatic straight through ball valve; and a bottom of the oil-gas separator is connected with a liquid storage tank through a manual valve;

further comprising a first circulation pump, a heat exchanger, a second circulation pump and a freezing machine; an inlet of the first circulation pump is connected with an oil outlet of the oil-gas separator; an outlet of the first circulation pump is connected with an oil inlet of the oil-gas separator and an oil inlet of the vacuum pump; an outlet pipeline of the first circulation pump further passes through a left heat exchange chamber of the heat exchanger; an inlet of the second circulation pump is connected with a coolant liquid outlet of the freezing machine; two by-passes are provided at an outlet of the second circulation pump, wherein one by-pass is connected with an inlet of a seventh pneumatic straight through ball valve, and the other by-pass is connected with coolant liquid inlets of the primary freezing tower and the secondary freezing tower; an outlet pipeline of the seventh pneumatic straight through ball valve penetrates a right heat exchanger chamber of the heat exchanger and is connected with a coolant liquid inlet of the freezing machine; and coolant liquid outlets of the primary freezing tower and the secondary freezing tower are further connected with the coolant liquid inlet of the freezing machine;

the coolant liquid inlet of the primary freezing tower is connected with the outlet of the second circulation pump through an eighth pneumatic straight through ball valve; a bottom end of the eighth pneumatic straight through ball valve is connected with an inlet of a third circulation pump; an outlet of the third circulation pump is connected with the coolant liquid outlet of the primary freezing tower, and a first temperature sensor is provided at the coolant liquid outlet of the primary freezing tower;

an inlet on the top left of the EO storage tank is connected with the bottom of the secondary cooling coil through a ninth pneumatic straight through ball valve, an EO buffer tank and a tenth pneumatic straight through ball valve successively; the position between the EO buffer tank and the tenth pneumatic straight through ball valve is further connected with a nitrogen storage tank through an eleventh pneumatic straight through ball valve; a top inlet of the EO storage tank is further connected with an outlet of the emit eliminator through a first pressure sensor and a twelfth pneumatic straight through ball valve; and a suspended electronic scale is provided on a top of the EO storage tank.

2. The ethylene oxide recycling system according to claim 1, wherein a connecting pipeline between an oil outlet of the vacuum pump and the oil-gas separator is connected with a nitrogen storage tank through a thirteenth pneumatic straight through ball valve; and a top of the activated carbon adsorption tank is further connected with the nitrogen storage tank through a fourteenth pneumatic straight through ball valve.

3. The ethylene oxide recycling system according to claim 2, wherein the fifth pneumatic straight through ball valve is connected with the gas inlet of the EO sterilization cabinet through a fifteenth pneumatic straight through ball valve and a vaporizer; a sixteenth pneumatic straight through ball valve is connected between the vaporizer and the fifteenth pneumatic straight through ball valve; the sixteenth pneumatic straight through ball valve is connected with a nitrogen storage tank through a seventeenth pneumatic straight through ball valve; a mixing tank and a second pressure sensor are further provided between the sixteenth pneumatic straight through ball valve and the seventeenth pneumatic straight through ball valve; and a position between the fifth pneumatic straight through ball valve and the fifteenth pneumatic straight through ball valve is further connected with an EO steel cylinder through an eighteenth pneumatic straight through ball valve and a nineteenth pneumatic straight through ball valve.

4. An ethylene oxide recycling system comprising: a sterilization cabinet, a vacuum pump, an oil-gas separator, a gas-liquid separator, a booster pump, a condensing tower, a storage tank, a freezing machine and a circulation pump; an exhaust outlet of the sterilization cabinet is connected with an inlet of the vacuum pump through a vacuum valve; an oil-gas outlet of the vacuum pump is connected with a top of the oil-gas separator; a return port of the vacuum pump is connected with a bottom of the oil-gas separator; a top outlet of the oil-gas separator is connected with an inlet of the gas-liquid separator; an outlet of the gas-liquid separator is connected with a left inlet of the condensing tower through the booster pump; a bottom inlet of the condensing tower is connected with the storage tank, an outlet of the storage tank is connected with a gas inlet of the sterilization cabinet; the oil-gas separator, the gas-liquid separator and the condensing tower are each provided with a cooling coil; an inlet of the circulation pump is connected with an outlet of the freezing machine; an outlet of the circulation pump is connected with one end of each cooling coil; and the other end of each cooling coil is connected with an inlet of the freezing machine.

5. The ethylene oxide recycling system according to claim 4, wherein a drainage pipeline is provided at a bottom of the oil-gas separator; a first pneumatic ball valve is provided in the drainage pipeline; a condensate water level electrode is provided in the drainage pipeline above the first pneumatic ball valve; and a temperature sensor is provided in the oil-gas separator.

6. The ethylene oxide recycling system according to claim 4, wherein a second pneumatic ball valve is provided in a connecting pipeline between the oil-gas separator and the gas-liquid separator; and the connecting pipeline between the second pneumatic ball valve and the oil-gas separator is connected with an external exhaust gas treatment unit through a first pressure sensor and a third pneumatic ball valve successively.

7. The ethylene oxide recycling system according to claim 4, wherein a fourth pneumatic ball valve is provided in a connecting pipeline between a bottom of the condensing tower and an inlet of the storage tank; a connecting pipeline between the fourth pneumatic ball valve and the storage tank is connected with a surge tank through a fifth pneumatic ball valve; two by-passes are provided on a top of the surge tank, one by-pass is connected with a right side of the condensing tower, and the other by-pass is connected with an external exhaust gas treatment unit through a sixth pneumatic ball valve; and a second pressure sensor is provided in a connecting pipeline between the condensing tower and the surge tank.

8. The ethylene oxide recycling system according to claim 4, wherein a top outlet of the storage tank is connected with a gas mixing module through a suspended electronic scale and a seventh pneumatic ball valve successively; the gas mixing module is connected with a gas inlet of the sterilization cabinet through a vaporizer; and a position between the seventh pneumatic ball valve and the suspended electronic scale is connected with an external nitrogen storage tank through an eighth pneumatic ball valve.

\* \* \* \* \*